United States Patent [19]
Hopkins et al.

[11] 4,064,455
[45] Dec. 20, 1977

[54] FLUID CONDITION MONITORING SYSTEM

[75] Inventors: Evan Lloyd Hopkins; Jerry Leslie Wedel, both of Emporia, Kans.

[73] Assignee: Hopkins Manufacturing Corporation, Emporia, Kans.

[21] Appl. No.: 742,781

[22] Filed: Nov. 18, 1976

[51] Int. Cl.² ............................................. G01R 27/26
[52] U.S. Cl. ................................ 324/61 R; 324/73 R; 340/20 D; 364/554
[58] Field of Search .......................... 324/61 R, 73 R; 340/200, 285; 235/151.31

[56] References Cited

U.S. PATENT DOCUMENTS

| | | | |
|---|---|---|---|
| 3,182,255 | 5/1965 | Hopkins et al. | 324/61 R |
| 3,330,159 | 7/1967 | Ongaro | 324/61 R X |
| 3,331,019 | 7/1967 | Irwin | 324/61 R |
| 3,984,766 | 10/1976 | Thornton | 324/61 R X |

*Primary Examiner*—Stanley T. Krawczewicz
*Attorney, Agent, or Firm*—Kenway & Jenney

[57] ABSTRACT

A system for monitoring the condition of a plurality of fluids as determined from measured electrical characteristics of samples of the fluids which are successively applied to a sensor. The system includes a remote test terminal having a remote controller and associated memory, a data entry device and display, and a test module. The test module includes the sensor and a coupled electrical circuit for generating a test signal representative of the electrical characteristics of a fluid sample applied to the sensor. The remote controller is responsive to a user operation at the data entry device to generate and store sample identification and period of use signals in the memory for each sample applied to a sensor, and to also control the test module to generate the test signal for the sample and to store that signal in the memory in conjunction with the sample identification and period of use signals.

14 Claims, 6 Drawing Figures

FLUID CONDITION MONITORING SYSTEM

REFERENCE TO RELATED PATENTS

The subject matter of this application is related to that of U.S. Pat. Nos. 3,182,255 and 3,331,019, and those patents are incorporated herein by reference.

BACKGROUND OF THE INVENTION

This invention relates to a system for monitoring the condition of a plurality of fluids, and more particularly, for determining the condition of the various fluids by measuring electrical characteristics of fluid samples and generating, storing, and monitoring historical record signals representative of the determined condition of the various fluids.

It is well known that the functional effectiveness of many commercially used fluids degrades substantially through use as the result of contaminants in the fluids. For example, lubricating oils lose their effectiveness in lubricating mechanical assemblies as contaminants such as dirt, water, acids, oxidation products, varnish, and anti-freeze enter the oil during use. In view of this, it has become common practice to frequently change the lubricating oil in many mechanical assemblies, such as internal combustion engines, in order to prolong the life of such mechanisms. For example, automobile manufacturers generally recommend a change of engine oil after a certain period of operation, typically 2,000 to 4,000 miles in order to maintain a relatively contaminant-free oil. However, that approach, whereby the oil is changed under a rigid use-related change schedule, does not accommodate variations in the rate at which the oil may be contaminated for individual engines, such as may be based on particular factors associated with the individual engines. As a result, the lubricating oil in many engines and other mechanical assemblies is often changed even though the original oil still has satisfactory lubricating properties, in one extreme, or, in the other extreme, at a time well beyond that where the oil has lost its lubricating properties, resulting in possible damage to the engine.

As a further example, the commercially used cooking oil in deep fat frying apparatus degrades through use due to the accumulation of contaminants such as dirt, water, food particles, and other debris. Typically, in commercial practice, the oil is replaced on a rigid, use-related change schedule, regardless of the actual condition of the oil.

In order to offset the inefficiencies of a rigid use-related schedule, instruments have been developed for testing the condition of such fluids by periodically sampling the fluid and measuring the contaminant level in the samples. By way of example, it is known that typical lubricating oils used in internal combustion engines may be characterized by a dielectric coefficient which is generally proportional to the concentration of suspended foreign matter (such as dirt, water, acids, varnish and anti-freeze) and the level of oxidation of the oil. Similarly, the dielectric coefficient of many commercial cooking oils are also proportional to the contaminant content of those oils. Accordingly, those dielectric coefficients may be considered as a measure of the contaminant level. U.S. Pats. Nos. 3,182,255 and 3,331,019 describe two such instruments suitable for measuring the dielectric coefficient of a sample of lubricating oil, and thereby provide a measure of the contaminant level of that sample.

While the instruments described by the above-referenced patents do set forth a sensor and coupled electrical circuit means to generate a test signal representative of the dielectric constant of a fluid sample applied to the sensor, those instruments only provide an indication of the contamination level for a single sample at a time. As a result, the use of these instruments often requires that extensive historical data records be maintained in order to efficiently maintain an on-going monitoring of the condition of fluids associated with a large number of assemblies. For example, individual vehicle lubricating oil condition records for truck fleets are often established with the manual recording of raw test data provided by the contaminant level measuring instruments. These records must then be tediously updated and monitored to identify those mechanical assemblies in which the lubricating oil contaminant level has passed a danger level.

Accordingly, it is an object of the present invention to provide a system for automatically monitoring the condition of a plurality of fluids, as determined from the measured electrical characteristics of samples of those fluids successively applied to a sensor.

It is another object of the present invention to provide a system whereby one or more remote test terminals may sample and generate test signals representative of the current characteristics of a plurality of fluids, and wherein those test terminals operate in conjunction with a central controller which maintains historical records for each of the fluids as obtained by interrogating the various remote terminals.

SUMMARY OF THE INVENTION

According to the present invention, a system is provided for monitoring the condition of a plurality of fluids, with the condition of the various fluids being determined from the measured characteristics of samples of the fluids successively applied to a sensor. The system comprises a remote test terminal, including the sensor and a coupled electrical bridge circuit, which is responsive to a user operation at an associated data entry terminal to generate and store a test signal representative of the dielectric coefficient of a sample together with sample identification and use signals representative of the identity of the fluid (or its source) and the period of use, respectively. For example, in a system for monitoring the condition of lubricating oil of a plurality of internal combustion engines, the user may successively apply oil samples from the various engines to the sensor, with each application being accompanied by the keyboard entry of data representative of an associated engine identification number as the sample identification signal, and data representative of the cumulative mileage or number of revolutions of the engine as the sample use signal. The test terminal responds to each set of entered signals to generate and store the test signal representative of the dielectric coefficient of the applied sample, together with the identification and period use signals.

The remote test terminal may also be used in conjunction with a central controller having a central memory for storing historical data records corresponding to each of the fluids being monitored, with each record including data representative of previously generated use and associated test signals generated for samples of the corresponding fluid. The central controller is selectively operative to interrogate the remote test terminals whereby the stored sample identification, use and associated test signals are transferred from the remote test terminal to the central memory. At the central controller, the historical records are continually monitored to identify those test signals which indicate that electrical characteristics of the corresponding fluid is within or without a predetermined range. For example, the central controller may continually monitor records of dielectric coefficient of lubricating oil in samples extracted from internal combustion engines to identify samples wherein the measured dielectric sample indicates that the contamination level of the oil is beyond a range where the oil functions as an effective lubricant.

In keeping with the present invention, each remote test terminal may be detachably coupled to the central controller, and include an associated rechargeable power supply. As a result, such a remote test terminal may readily be detached from the central controller, permitting use at diverse locations. When the remote test terminal is then coupled back to the central controller, the terminal may readily be interrogated to transfer the stored sample identification, use and test signals to the central controller for monitoring in the same manner outlined above. This aspect of the present invention is particularly advantageous in the monitoring of lubricating oil condition in motor vehicle engines whereby a compact, highly mobile test terminal may be carried from vehicle to vehicle gathering sample data and then returned to the relatively immobile central controller for historical record updating and monitoring. With this system configuration, remote test terminals may be located at dispersed service stations which include suitable modem equipment so that the test terminals may be interrogated by the central controller over a standard telephone link. As a result, the lubrication oil condition for the various vehicles may be monitored without constraining each vehicle to frequently return to a single service station.

In addition, one or more assemblies (e.g. engines) may have an associated mobile recorder which may be interconnectable with both the remote test terminal and central controller. When connected to the remote test terminal, the mobile recorder may store the sample use and associated test signals generated by the remote test station. When interconnected with the central controller, the mobile recorder may be interrogated whereby the stored sample use and test signals may be transferred together with identification signals from the mobile recorder to the central memory where the data is added to the historical record corresponding to that fluid. Again, this aspect of the invention is particularly advantageous in the monitoring of lubricating oil condition in motor vehicle engines. For example, remote test terminals may be located at dispersed service stations which are not in communication with the central controller and which function only as stations for testing a sample and establishing a temporary record in the mobile recorder. In this configuration, at least one communication station may be used to couple the mobile recorder to the central controller, thereby permitting an update and monitoring of the historical record. This configuration permits the use of a network of relatively inexpensive test stations in conjunction with a single communication station and central controller.

Alternatively, the mobile recorder may maintain a historical record for its associated vehicle and a plurality of central controllers may be located at dispersed service stations, with the central controllers merely functioning to review the historical record of a connected mobile recorder, again permitting the use of a network of inexpensive test stations with a relatively small network of more expensive communication stations and central controllers.

BRIEF DESCRIPTION OF THE DRAWINGS

The foregoing and other objects of this invention, the various features thereof, as well as the invention itself, may be more fully understood from the following description when read together with the accompanying drawings in which.

DESCRIPTION OF THE PREFERRED EMBODIMENT

Figure 1:
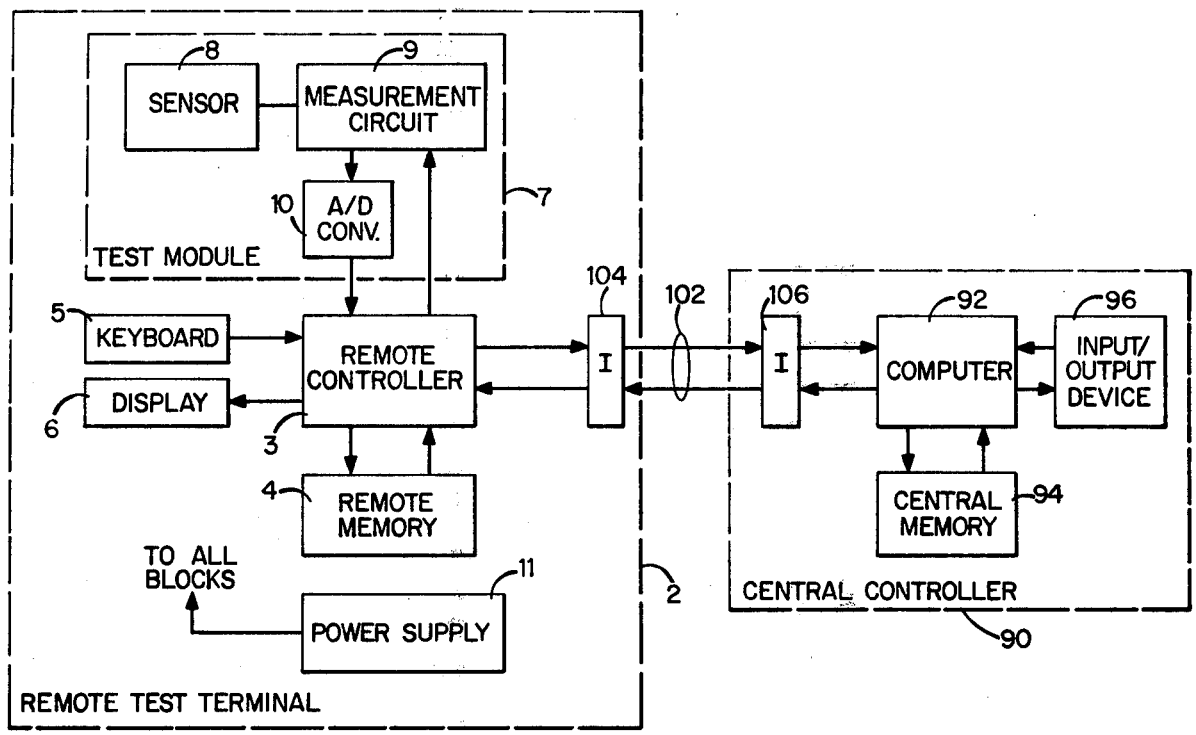
FIG. 1 shows, in block diagram form, a system in accordance with the present invention.
Figure 2:
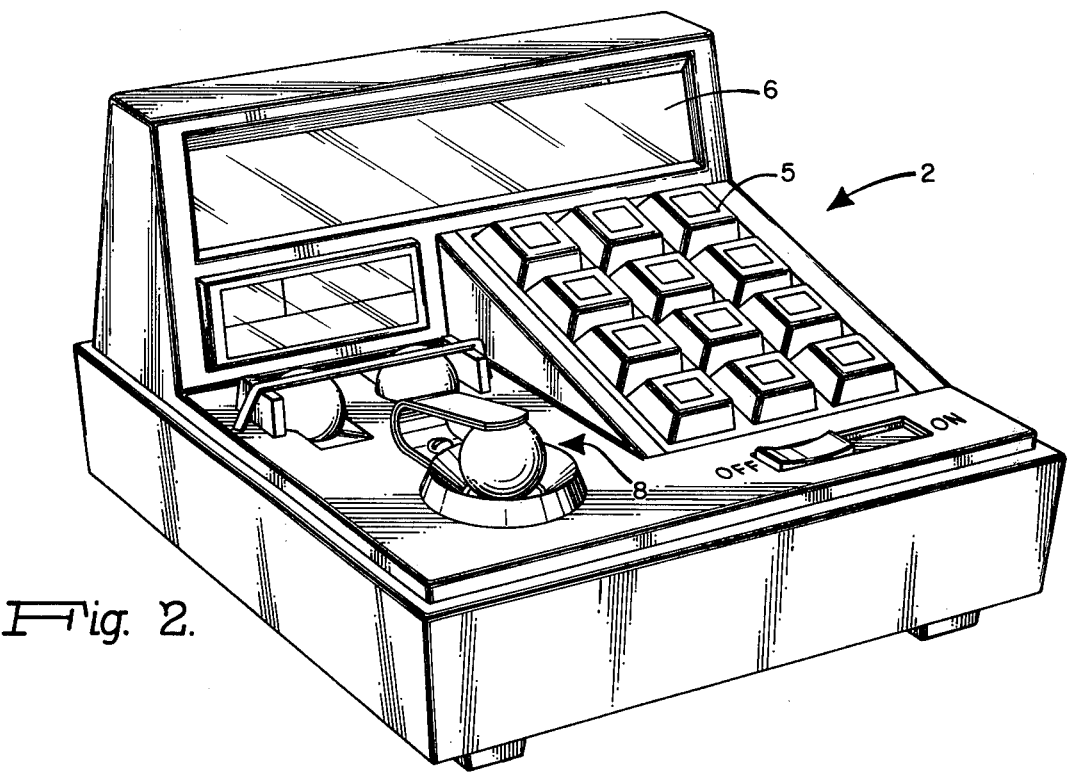
FIG. 2 shows an exemplary remote test terminal for the system of FIG. 1.
Figure 3:
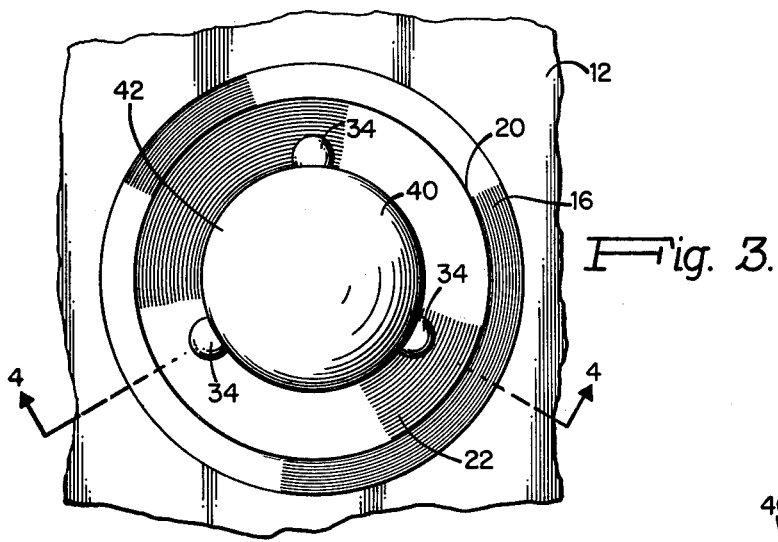
FIGS. 3 and 4 show a top plan and sectional view, respectively, of the sensor of the remote test terminal in FIG. 1.
Figure 4:
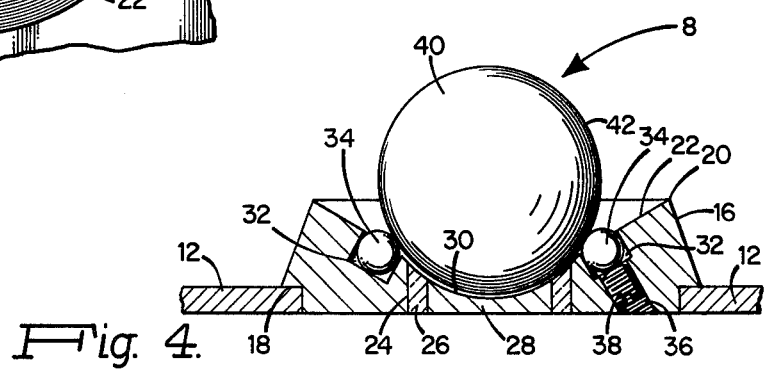

FIG. 1 shows an embodiment of the present invention in block diagram form. In that figure, a remote test terminal 2 is illustrated with an associated remote controller 3, interconnected with remote memory 4, data entry device 5, data display device 6, test module 7 and power supply 11. The test module 7 includes a sensor 8, measurement circuit 9, and an analog-to-digital converter 10. An illustrative form for the remote test terminal 2 is shown in FIG. 2. The sensor 8 of the terminal of FIG. 2 is illustrated in plan and sectional view in FIGS. 3 and 4, respectively, and an exemplary measurement circuit 9 is illustrated in schematic form in FIG. 5. The sensors and measurement circuits of U.S. Pat. Nos. 3,182,255 and 3,331,019 are suitable for use with the present invention and, accordingly, FIGS. 2 and 3 of U.S. Pat. No. 3,331,019 are incorporated in the present application as FIGS. 4 and 5, respectively, with the elements of FIGS. 3–5 having identical reference designations as the corresponding elements in FIGS. 2 and 3 of U.S. Pat. No. 3,331,019.

As described fully in the incorporated reference, the illustrated sensor 8 includes a first member 28 forming a receptacle for a sample of fluid to be tested. Member 28 includes an electrically conductive, spherically concave surface portion 30 characterized by a first radius of curvature. The sensor also includes a second member 40 having an electrically conductive, spherically convex surface portion 42 characterized by a second radius of curvature, with the second radius being less than the first radius. As illustrated, the second member 40 is in the form of a conductive sphere. The sensor 8 further includes a means for supporting the members 28 and 40 so that a conductive, concave portion of member 28 is opposite to and spaced from a conductive, convex portion of member 40 by a gap to form an electrical cell having a region for retaining a sample of fluid between those portions.

As illustrated, the sensor 8 includes an electrically conductive, annular ring 26 seated in a top wall 12 of the terminal 2 with three spherical support balls 34 providing a three-point support for the spherical member 40. The member 30 is supported with respect to the ring 16 by an annular dielectric spacer 26 positioned between member 30 and ring 16. The cell formed by members 28 and 40 is nominally a parallel plate capacitor, although the actual separation between the opposed concave and convex surfaces may be adjusted by varying the set screw 38 which in turn controls the position of the adjacent support ball 34.

Figure 5:
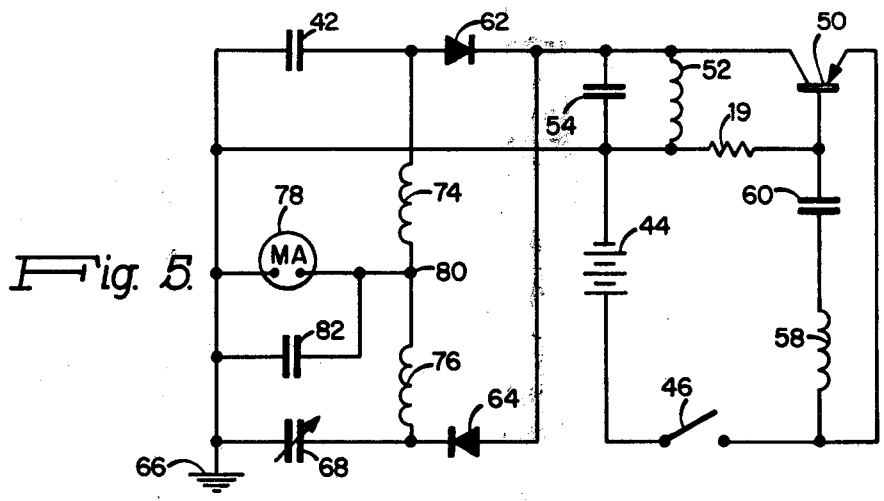
FIG. 5 shows, in schematic form, an exemplary measurement circuit for the remote test terminal of FIG. 1.

The exemplary measurement circuit 9 shown in FIG. 5 includes a radio frequency oscillator which supplies power by way of diodes 62 and 64 to a bridge circuit made up by capacitors 42 and 68 and substantially identical coils 74 and 76. The variable capacitor 68 in FIG. 5 corresponds to the sensor 8 illustrated in FIGS. 3 and 4, with its capacitance being a function of the dielectric coefficient to the medium between members 28 and 40 for a particular separation as established by set screw 38. The capacitor 42 is selected so that the sensor 8 may be adjusted (by means of set screw 38) so that the characteristic capacitance of sensor 8 is substantially the same as that for capacitor 42 when a calibration fluid is in the gap between members 28 and 40. The meter 78 provides an indication of the unbalance of the bridge circuit. In the embodiment of FIGS. 1 and 2, the meter 78 is replaced by the analog-to-digital converter 10 and the digital readout 6 so as to provide a digital indication of the balance condition of the bridge circuit. Of course, the circuit of FIG. 5 is merely exemplary and other well known capacitive bridge circuits may readily be used.

In operation, with a sample to be tested in the region between members 28 and 40, the bridge circuit may enter an unbalanced state due to the difference in dielectric coefficient between the sample and the reference oil with which the bridge was calibrated. The reading provided by meter 78 (or display 6) provides a measure of that difference in the dielectric coefficient.

In the preferred embodiment, the remote controller 3 of terminal 2 is a microprocessor having an associated program memory. By way of example, the controller 3 and memory 4 comprise a type CDP 1802 CD microsensor and type CDP 1802 CD memory manufactured by RCA, Somerville, New Jersey; the keyboard 5 comprises a model 12-PX1-1 manufactured by the Micro Switch division of Honeywell, Freeport, Illinois; and the display 6 comprises a liquid crystal display type R-TA-8094T manufactured by RCA, Somerville, New Jersey.

Under the control of the microprocessor of controller 3, the remote test terminal 2 operates in conjunction with the random access (remote) memory 4 and test module 7 in a manner responsive to a user keyboard entry at device 5 of a digital sample identification signal and period of use signal. The micropressor directs the storage of the sample identification signal and use signal in memory 4 and also directs the test module 7 to generate a digital test signal representative of the dielectric coefficient of a sample in sensor 8 and to transfer that test signal to the remote memory 4 for storage at a location associated with the stored sample identification and use signals. In some embodiments, the controller 3 may provide an in situ comparison of the test signal with a predetermined value stored in memory 4 to immediately evaluate the condition of the tested fluid. In other embodiments, the raw data test signal may be stored in memory until retrieved by a central controller, such as described more fully below, for evaluation at a central station.

Also shown in FIG. 1 is a central controller 90 comprising a computer 92 and associated central memory 94 and input/output device 96. By way of example, the computer 92, memory 94 and input/output device comprise a type 8080A microprocessor, type 2101 MOS RAM, and type 8255 (PPI) PORT, respectively, all manufactured by Intel Corporation, Santa Clara, California. The input/output device 96 may further include conventional data terminal devices such as a teletype, CRT display, or printer.

The central controller 90 is coupled to the remote controller 3 of terminal 2 by way of communication link 102 and terminal interface 104 of terminal 2, and central controller interface 106 of controller 96. The interfaces 104 and 106 include modem equipment of conventional form, with the interface 104 being configured so that the remote test terminal 2 may be detachably connected to the communication link 102.

In operation, the remote controller 3 sets a data ready flag following the storage of new sample identification, use and test signals in memory 4. When remote controller 3 is coupled to computer 92 of controller 90, computer 92 identifies that flag and initiates a data transfer operation whereby the microprocessor of controller 3 retrieves the stored identification, use and test signal data from the remote memory 4 and transfers that data by way of link 102 to computer 92. Computer 92 in turn monitors the identification signals of the incoming data from terminal 2 and sorts and updates the corresponding historical records stored within memory 94 with the transferred use and test signal data. Between interrogations, the computer 92 continuously scans the stored historical records in memory 94 to identify those records which include test data indicative of undesirable electrical characteristic, e.g. dielectric coefficient, for the associated fluid. Upon the identificaton of such a historical record, computer 92 provides an indication of this condition at the central controller by way of device 96. In alternative embodiments, the system may be programmed using conventional techniques to that graphical displays of the historical record data may be generated at either or both of device 96 and display 6.

Figure 6:
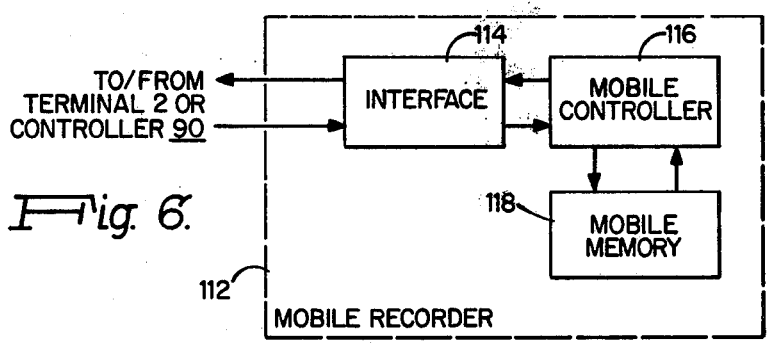
FIG. 6 shows, in block diagram form, a mobile record for use with the system of FIG. 1 in accordance with the present invention.

FIG. 6 illustrates a mobile recorder 112 which is suitable for use with the system illustrated in FIG. 1 and wherein the mobile recorder 112 is adapted to be transported with a particular vehicle. Mobile recorder 112 includes means for interconnection with remote test terminal 2 and central controller 90 by way of interface 114, and further includes a mobile controller 116 and a mobile memory 118. The mobile controller 116 comprises a microprocessor with an associated program memory including a permanently stored mobile identification signal representative of the vehicle to which the recorder is attached.

In operation, when recorder 112 is interconnected with terminal 2, remote controller 3 directs the transfer of stored period of use and test data from the remote memory 4 to the mobile memory 118 and sets a data ready flag. When the mobile recorder 112 is interconnected with the central controller 90, the computer 92 may identify the flag and control the transfer of the stored data from mobile memory 118 to the central memory 94 so that the data may be utilized to augment the historical data record in memory 94 whereby that historical data record may be monitored as described above.

When the mobile recorder 112 is interconnected with the central controller 90 in alternative embodiments, wherein the mobile recorder is utilized as the permanent historical data record for its attached vehicle, the computer 92 may direct the transfer of data representative of that stored in memory 118 to memory 94 and then process that data to identify a dangerous fluid condition.

While in the presently-described embodiment, the mobile memory 118 may be a random-access memory which operates in conjunction with a microprocessor in mobile controller 116, other embodiments might utilize a magnetic tape cassette and an associated cassette drive as the memory 118. By way of example, a Type Beta 326/392 system, manufactured by Monroe, Morris Plains, New Jersey, is suitable for such embodiments. With such a programmable mobile controller, custom programs may readily be generated and used for individual vehicle in a fleet, thereby providing substantial system flexibility. Furthermore, other embodiments may utilize the mobile recorder 112 in conjunction with an input/output device in order to store further data (e.g. oil change data, engine operating conditions) in addition to the stored period of use and test data. As further examples, the recorder 112 may also store data representative of tire wear, tire installation data, gas mileages, temperature conditions in refrigeration units on the respective vehicles, and velocity and other driving statistics.

SUMMARY OF THE ADVANTAGES AND SCOPE OF THE INVENTION

The present invention provides a system for automatically monitoring the condition of a plurality of fluids or other parameters of one or more vehicles or devices. In one form, the invention includes one or more test terminals for remotely evaluating the condition of fluids from a succession of applied samples, and further includes a central controller for establishing, continually updating, and monitoring historical records based on the evaluated conditions as obtained by interrogating the various remote terminals.

In some forms of this invention, the remote terminals may be hardwired to the central controller, and in other forms the terminals may be linked by conventional modems and data transfer equipment. The remote terminals may be configured with local memory capability so that a relatively large amount of condition data may be gathered prior to transfer to the historical record sub-system in response to either periodic or requested interrogation commmands. Alternative embodiments may utilize remote terminals with local historical record memories which may be periodically updated by command signals from a central control system.

The invention may be used for the evaluation of fluids whose condition may be characterized by an electrical characteristic, as exemplified by the dielectric coefficient of lubricating oils or cooking oils. In this form, the fluid condition measuring sensors and circuit are integrated into a highly efficient data processing sub-system to provide remote fluid condition data which may readily be transferred to a central data processing sub-system for detailed analysis appropriate for historical record creation and monitoring.

In other forms of the invention, other vehicle or device parameters may be monitored using appropriate sensors, measuirng circuits, and constructing and monitoring similar historical records.

With this invention, the data gathering for the monitoring may be accomplished at relatively inexpensive and versatile remote terminals which may be interrogated by a record-keeping sub-system, thereby permitting efficient monitoring of a widely dispersed subject, such as individual motor vehicles within a fleet, without requiring return to a common service point.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A system for monitoring the condition of a plurality of fluids as determined from measured electrical characteristics of samples of said fluids successively applied to a sensor, comprising:

a remote test terminal having a remote controller and associated remote memory, a data entry means and a test module, said test module including said sensor and a coupled electrical circuit means to remotely generate a test signal representative of said electrical characteristic of said samples.

wherein said remote controller includes means responsive to a user operation at said data entry means to generate and store associated sample identification and use signals in said remote memory for each sample applied to said sensor, said sample identification signal being representative of the identity of the fluid for said sample under test, and said associated use signal being representative of the period of use of said sample, and wherein said remote controller further includes means responsive to said user operation to control and test module to generate said test signal for said sample, and means to store said test signal in said remote memory in association with said stored sample identification and use signals, and a test signal monitoring means for automatically identifying fluids for which said test signals indicate a predetermined condition, thereby providing evaluation of said remotely generated test signals representative of the condition of said fluids.

2. A system according to claim 1 wherein said test signal monitoring means comprises:

a central controller coupled to said remote test terminal, said central controller including an associated central memory having stored historical data records, each record corresponding to one of said plurality of fluids and including data representative of said use and associated test signals generated for samples of said corresponding fluid, and selectively operative means to interrogate said remote test terminal whereby said stored use and associated test signals are transferred from said remote memory to said central memory and stored therein in association with the historical records of the corresponding fluids.

3. A system for monitoring the condition of a plurality of fluids as determined from measured electrical characteristics of samples of said fluids successively applied to a sensor, comprising:

a remote test terminal having a remote controller and associated remote memory, a data entry means, and test module, said test module including said sensor and a coupled electrical circuit means to remotely generate a test signal representative of said electrical characteristic of said samples, said sensor including a first member forming a receptacle for a sample of fluid to be tested, said first member including an electrically conductive, spherically concave surface portion characterized by a first radius of curvature, a second member including an electrically conductive, spherically convex surface portion characterized by a second radius of curvature, said second radius being less than said first radius, a support means for supporting said first and second members whereby said concave portion of said first member is opposite and spaced from said convex portion of said second member by a gap to form an electrical cell having a region for retaining a sample of fluid between said conductive portions of said first and second members, wherein said remote controller includes means responsive to a user operation at said data entry means to generate and store associated sample identification and use signals in said remote memory for each sample applied to said sensor, said sample identification signal being representative of the identity of the fluid for said sample under test, and said associated use signal being representative of the period of use of said sample, and wherein said remote controller further includes means responsive to said user operation to control said test module to generate said test signal for said sample, and means to store said test signal in said remote memory in association with said stored sample identification and use signals, and a test signal monitoring means for automatically identifying fluids for which said test signals indicate a predetermined condition, thereby providing evaluation of said remotely generated test signals representative of the condition of said fluids.

4. A system according to claim 3 wherein said test signal monitoring means comprises:

a central controller coupled to said remote test terminal, said central controller including an associated central memory having stored historical data records, each record corresponding to one of said plurality of fluids and including data representative of said use and associated test signals generated for samples of said corresponding fluid, and selectively operative means to interrogate said remote test terminal whereby said stored use and associated test signals are transferred from said remote memory to said central memory and stored therein in association with the historical records of the corresponding fluids.

5. A system according to claim 4 wherein said central controller further comprises means to identify historical records in which a value of said electrical characteristic represented by test signal data included therein is within a predetermined range.

6. A system according to claim 5 wherein said central controller further comprises means to identify historical records in which a value of said electrical characteristic represented by the data included therein is outside said predetermined range, and means to indicate the identity of such records.

7. A system according to claim 4 wherein said central controller further comprises means to identify historical records in which the most recent value of said electrical characteristic represented by the data included therein differs from the oldest corresponding value of said record by a predetermined value, and means to indicate the identity of such records.

8. A system according to claim 4 wherein said central controller further comprises means to identify times when said remote test terminal is coupled thereto.

9. A system according to claim 4 wherein said remote test terminal further comprises means for detachably coupling said terminal to said central controller.

10. A system according to claim 9 wherein said remote test terminal further comprises a rechargeable power supply operative when said terminal is detached from said central controller.

11. A system according to claim 4 further comprising a mobile record means associated with at least one of said fluids, said mobile record means including means for detachable interconnection with said remote test terminal and said central controller, and mobile memory means for storing a sample identification signal representative of the identity of said fluid, and for storing said use and associated test signals when said mobile record means is interconnected with said remote test terminal, and wherein said central controller includes selectively operative means to interrogate said mobile record means whereby said stored sample identification, use and test signals are transferred from said mobile memory means to said central memory and stored therein in association with the historical record corresponding to said fluid.

12. A system according to claim 3 wherein said plurality fluids are lubricating oils in a corresponding plurality of internal combustion engines, and each of said sample identification signals is representative of the identity of the engine from which said sample was extracted and each of said use signal is representative of the period of use of said said sample in said engine when extracted.

13. A system according to claim 3 wherein said sensor and coupled electrical circuit means comprise a bridge circuit.

14. A system according to claim 3 wherein said remote test terminal further has a display means, and said remote controller further includes means to control said display means to display signals representative of said test signals.

* * * * *